United States Patent
Sheshbaradaran

(10) Patent No.: US 11,135,212 B2
(45) Date of Patent: *Oct. 5, 2021

(54) METHOD FOR TREATING OSTEOPOROSIS, OSTEOPENIA OR LOW BONE MINERAL DENSITY

(71) Applicant: Altum Pharmaceuticals Inc., Vancouver (CA)

(72) Inventor: Hooshmand Sheshbaradaran, Hoboken, NJ (US)

(73) Assignee: Altum Pharmaceuticals Inc., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/670,970

(22) Filed: Oct. 31, 2019

(65) Prior Publication Data
US 2020/0061048 A1    Feb. 27, 2020

Related U.S. Application Data

(63) Continuation of application No. 15/668,607, filed on Aug. 3, 2017, now Pat. No. 10,463,657, which is a
(Continued)

(51) Int. Cl.
| | |
|---|---|
| *A61K 33/24* | (2019.01) |
| *A61K 31/47* | (2006.01) |
| *A61P 35/04* | (2006.01) |
| *A61P 19/10* | (2006.01) |
| *A61K 31/555* | (2006.01) |
| *A61P 19/08* | (2006.01) |
| *C07F 5/00* | (2006.01) |
| *A61K 31/00* | (2006.01) |
| *A61K 33/00* | (2006.01) |

(52) U.S. Cl.
CPC .......... *A61K 31/47* (2013.01); *A61K 31/555* (2013.01); *A61K 33/24* (2013.01); *A61P 19/08* (2018.01); *A61P 19/10* (2018.01); *C07F 5/003* (2013.01); *A61K 31/00* (2013.01); *A61K 33/00* (2013.01); *A61P 35/04* (2018.01); *C07F 5/00* (2013.01)

(58) Field of Classification Search
CPC ...... A61K 31/47; A61K 31/555; A61K 33/24; A61P 35/04
See application file for complete search history.

(56) References Cited

U.S. PATENT DOCUMENTS 9,725,471 B2 * 8/2017 Sheshbaradaran ..... A61K 31/47

FOREIGN PATENT DOCUMENTS

WO  WO-2008036429 A1 * 3/2008 ............. A61P 35/00

OTHER PUBLICATIONS

Collery et al., "Preclinical toxicology and tissue gallium distribution of a novel antitumour gallium compound: tris (8-quinolinolato) gallium (III)," Anticancer Res. 1996;16(2):687-91. PMID: 8687115. (Year: 1996).*

(Continued)

*Primary Examiner* — Theodore R. Howell
(74) *Attorney, Agent, or Firm* — Brunet & Co. Ltd.; Robert Brunet; Hans Koenig

(57) ABSTRACT

A method for treating osteoporosis and related methods are disclosed. The methods generally comprise administering to a patient in need of treatment an effective amount of tris(8-quinolinolato)gallium(III) or an analog thereof.

2 Claims, 4 Drawing Sheets

Related U.S. Application Data continuation of application No. 13/957,503, filed on Aug. 2, 2013, now Pat. No. 9,725,471, which is a continuation of application No. 13/249,248, filed on Sep. 30, 2011, now abandoned, which is a continuation of application No. PCT/US2010/029285, filed on Mar. 30, 2010.

(60) Provisional application No. 61/164,856, filed on Mar. 30, 2009.

(56) References Cited

OTHER PUBLICATIONS

Collery et al., "Gallium in cancer treatment," Grit. Rev. Oncol. Hematol. 42(3):283-96. PMID: 12050020. (Year: 2002).*
Timerbaev AR, et al. J. Sep. Sci. 2007, 30, 399-406.
Rudnev, AV, et al. Journal of Inorganic Biochemistry. 100 (2006) 1819-1826.
NCI Results for NKP-46—The Standard Agents.
Hummer AA, et al. J. Med. Chem. 2012, 55, 5601-5613.
Enyedy EA, et al. Journal of Inorganic Biochemistry. 117 (2012) 189-197.
Chen D, et al. Cancer Res. 2007, 67(19), 9258-9265.
Baerga R, et al. 2012 AACR Meeting, Poster Presentation, NKP-2235 exhibits synergistic activity in preclinical in vitro models with a broad range of anti-tumor agents.

* cited by examiner

METHOD FOR TREATING OSTEOPOROSIS, OSTEOPENIA OR LOW BONE MINERAL DENSITY

RELATED PATENT APPLICATIONS

This application is a continuation of U.S. patent application Ser. No. 15/668,607, filed on Aug. 3, 2017, now U.S. Pat. No. 10,463,657, to be issued Nov. 5, 2019; which is a continuation of U.S. patent application Ser. No. 13/957,503, filed on Aug. 2, 2013, now U.S. Pat. No. 9,725,471, issued Aug. 8, 2017; which is a continuation of U.S. patent application Ser. No. 13/249,248, filed on Sep. 30, 2011, now abandoned; which is a continuation of PCT/US2010/029285 filed on Mar. 30, 2010 which claims the benefit and priority of U.S. Provisional Application No. 61/164,856 filed on Mar. 30, 2009, the entirety of each is hereby incorporated by reference.

FIELD OF THE INVENTION

The present invention generally relates to methods of treating diseases, and particularly to a method of treating osteoporosis and related disorders.

BACKGROUND OF THE INVENTION

Osteoporosis is a major health problem afflicting millions of people worldwide. It is most prevalent in postmenopausal women, but also occurs in a significant portion of men over the age of 50. In patients on glucocorticoids, and those undergoing hormone ablation therapy for either prostate or breast cancer, bone loss and osteoporosis are especially significant. In osteoporosis patients, the decrease of bone mineral density (BMD) and bone mass content (BMC) result in increased bone fragility and risk of bone fracture. Osteoporosis may significantly affect life expectancy and quality of life.

Estrogen replacement therapy was the main approach for a long time in postmenopausal women for preventing osteoporosis until it was discovered to be associated with an increased incidence of cancer. See e.g., Prentice et al., *Am. J. Epidemiol.*, 170(1): 12-23 (2009). Bisphosphonates were first developed in mid 1990s and have become the main pharmaceutical measures for osteoporosis. However, oral bisphosphonates are poorly absorbed and are often associated with esophageal inflammation. Recently, RANKL-targeting antibodies such as denosumab have shown some promise as effective agents in reducing bone resorption. See e.g., McClung et al., *N. Engl. J. Med.*, 354(8):821-31 (2006).

SUMMARY OF THE INVENTION

It has been surprisingly discovered that tris(8-quinolinolato)gallium(III) is effective in inhibiting osteoclastic bone resorption, reducing bone loss, and treating osteoporosis. Accordingly, in a first aspect, the present invention provides a method of reducing osteoclastic bone resorption in a patient comprising administering to a patient in need of treatment an osteoclastic bone resorption-inhibiting amount of a compound according to Formula (I) below or a pharmaceutically acceptable salt thereof (e.g., tris(8-quinolinolato)gallium(III)).

In a second aspect, a method of treating osteoporosis is provided comprising administering to a patient in need of treatment a therapeutically effective amount of a compound according to Formula (I) below or a pharmaceutically acceptable salt thereof (e.g., tris(8-quinolinolato)gallium (III)). In one embodiment, the method is used to treat or prevent postmenopausal osteoporosis (PMO) in women. In another embodiment, the method is used to treat, prevent, or reduce the risk or incidence of, bone loss or skeletal-related events (such as bone fractures) in patients undergoing hormone ablation therapy for either prostate or breast cancer. In yet another embodiment, the method is used for the prevention and treatment of glucocorticoid-induced osteoporosis (GIO) in men and women who are either initiating or continuing systemic glucocorticoid treatment.

In yet another aspect, the present invention provides a method of treating Paget's disease by administering to a patient in need of treatment a therapeutically effective amount of a compound according to Formula (I) below or a pharmaceutically acceptable salt thereof (e.g., tris(8-quinolinolato)gallium(III)).

Additionally, the present invention also provides a method of preventing, or delaying the onset of, bone metastasis of cancer comprising administering an effective amount of a compound of Formula (I) or a pharmaceutically acceptable salt thereof (e.g., tris(8-quinolinolato)gallium(III)) to a patient identified as, or diagnosed of, having cancer (e.g., lung cancer, breast cancer, prostate cancer, lymphoma or multiple myeloma) but without bone metastasis, thereby preventing, or delaying the onset of, cancer bone metastasis.

The present invention further provides a method of treating, preventing, or reducing the risk or incidence of, bone loss or skeletal-related events (such as bone fractures) in patients having cancer with bone metastasis comprising identifying a patient having a cancer that has metastasized to bone, and administering a therapeutically effective amount of a compound of Formula (I) or a pharmaceutically acceptable salt thereof (e.g., tris(8-quinolinolato)gallium(III)) to the patient.

In yet another aspect, the present invention provides a method of treating, preventing, or reducing the risk or incidence of, bone loss or skeletal-related events (such as bone fractures) in patients having neuroendocrine tumors by administering to a patient in need of treatment a therapeutically effective amount of a compound according to Formula (I) below or a pharmaceutically acceptable salt thereof (e.g., tris(8-quinolinolato)gallium(III)).

The present invention further provides a method of treating cancer with bone metastasis comprising identifying a patient having a cancer that has metastasized to bone, and administering a therapeutically effective amount of a compound of Formula (I) or a pharmaceutically acceptable salt thereof (e.g., tris(8-quinolinolato)gallium(III)) to the patient.

In another aspect, the present invention provides a use of a compound according to Formula (I) below or a pharmaceutically acceptable salt thereof (e.g., tris(8-quinolinolato) gallium(III)) for the manufacture of a medicament useful for reducing osteoclastic bone resorption, treating, preventing or delaying the onset of osteoporosis, treating or preventing or delaying the onset of Paget's disease, or treating, preventing, or delaying the onset of, bone metastasis of cancer, or treating a cancer with bone metastasis.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

Figure 1:
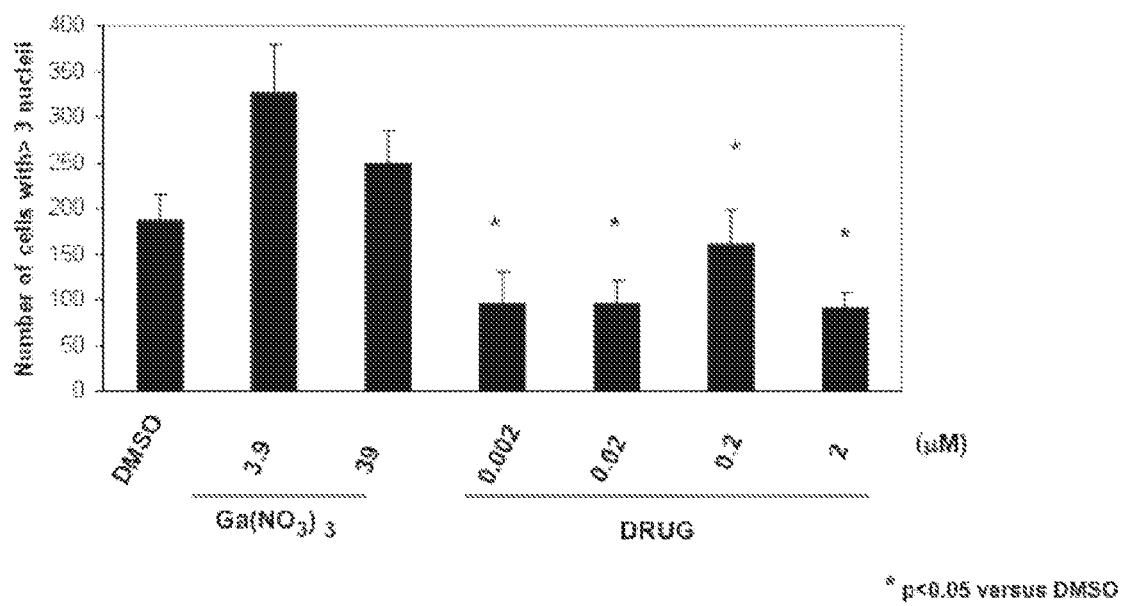
FIG. 1 is a graph demonstrating that treatment with tris(8-quinolinolato)gallium(III) inhibited osteoclast differentiation.

The present invention is in part based on the discovery that the compound tris(8-quinolinolato)gallium(III) is particularly effective in inhibiting osteoclast maturation or formation, reducing bone resorption, preventing bone loss, thereby maintaining or increasing bone mineral density in mammals.

Accordingly, in a first aspect, the present invention provides a method of reducing osteoclastic bone resorption in a patient comprising treating a patient in need of treatment, with an osteoclastic bone resorption-inhibiting amount of a gallium complex of Formula (I)

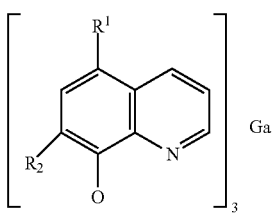

wherein $R^1$ represents hydrogen, a halogen or a sulfono group $SO_3M$, in which M is a metal ion, and $R^2$ represents hydrogen, or $R^1$ is Cl and $R^2$ is I, or a pharmaceutically acceptable salt thereof. The method can result in the reduction of osteoclastic bone resorption and alleviation of the associated symptoms, such as skeletal-related events (e.g., bone loss and/or decrease of bone mineral density). That is, the present invention is directed to the use of an effective amount of a compound according to Formula (I) or a pharmaceutically acceptable salt thereof for the manufacture of medicaments for reducing osteoclastic bone resorption, preventing or slowing bone loss, preventing or slowing the decrease of bone mineral density, or preventing or reducing the incidence of skeletal-related events (e.g., bone fractures, bone loss, etc.) in mammals including humans.

In preferred embodiments, the gallium complex is tris(8-quinolinolato)gallium(III)

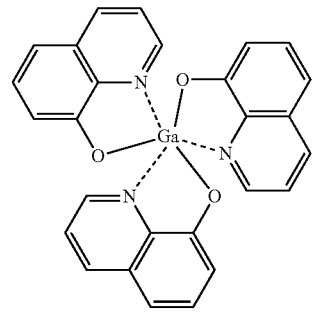

or a pharmaceutically acceptable salt thereof.

In another aspect, the present invention provides a method of treating, preventing or delaying the onset of, osteoporosis. The method comprises treating a patient in need of the treating, preventing or delaying the onset, with a therapeutically effective amount of a gallium complex of Formula (I)

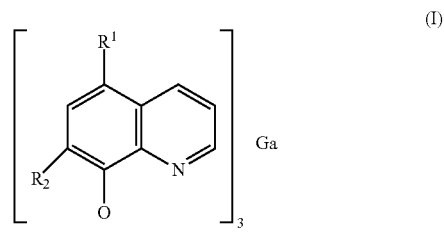

wherein $R^1$ represents hydrogen, a halogen or a sulfono group $SO_3M$, in which M is a metal ion, and $R^2$ represents hydrogen, or $R^1$ is Cl and $R^2$ is I, or a pharmaceutically acceptable salt thereof. That is, the present invention is directed to the use of an effective amount of a compound according to Formula (I) or a pharmaceutically acceptable salt thereof for the manufacture of medicaments for treating, preventing or delaying the onset of osteoporosis.

In preferred embodiments, the gallium complex is tris(8-quinolinolato)gallium(III)

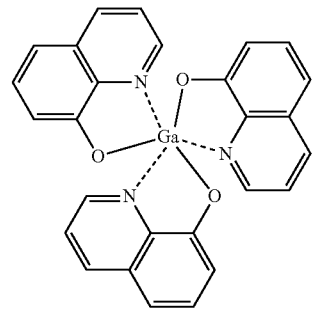

or a pharmaceutically acceptable salt thereof.

Thus, the present invention provides a method of treating osteoporosis or osteopenia comprising treating a patient in need of treatment with a therapeutically effective amount of tris(8-quinolinolato)gallium(III). The present invention also provides a method of slowing down the decrease of bone mineral density, delaying the onset of osteoporosis, or increasing bone mineral density in a patient in need of such treatment (e.g., those having a tendency or increased risk of developing osteoporosis) comprising treating the patient with tris(8-quinolinolato)gallium(III) at an amount sufficient to slowing down the decrease of bone mineral density, increasing bone mineral density, increasing bone mass content, or delaying the onset of osteoporosis.

Osteoporosis is generally characterized by generalized bone loss or low bone mineral density. The methods of the present invention is useful in treating or delaying the onset of any generalized bone loss or low mineral density, including, but not limited to, osteoporosis, such as postmenopausal osteoporosis, steroid- or glucocorticoid-induced osteoporosis, age-related osteoporosis, osteoporosis induced by rheumatoid arthritis or by cancer, osteomalacia, idiopathic osteoporosis, or Paget's disease.

In various embodiments of the various methods of the present invention, optionally a step of identifying a patient in need of treatment or prevention can be included. For example, patients having osteoporosis or osteopenia or low bone mineral density can be diagnosed by any diagnosis methods or criteria in the art, e.g., by measuring the bone mineral density (BMD), using, e.g., dual energy X-ray absorptiometry (DXA or DEXA), serum markers, X-rays, etc.

Also, the identification of patients at risk of developing osteoporosis or generalized or local bone loss is generally known in the art. For example, patients having risk factors that are typically associated with an increased likelihood of bone loss and of developing osteoporosis can be identified. Known risk factors for osteoporosis include, but are not limited to, post-menopause, steroid or glucocorticoid use, age particularly in females, diseases such as rheumatoid arthritis, osteomalacia, and Paget's disease, periodontal disease, bone fracture, and periprosthetic osteolysis. In addition, patients having certain types of cancer (e.g., lung cancer, breast cancer, prostate cancer, multiple myeloma or neuroendocrine tumors) with or without bone metastasis, and patients undergoing hormone ablation therapy for either prostate or breast cancer, are all at risk of bone loss, bone fractures, increased frequency of skeletal-related events, and osteoporosis.

Thus, in some embodiments, the methods of the present invention are used for treating, or preventing or delaying the onset of, postmenopausal osteoporosis (PMO) in women by administering a compound of Formula (I) (e.g., tris(8-quinolinolato)gallium(III)) to a women in need of such treatment, prevention or delay. In other embodiments, the methods are used to reduce the risk or incidence of bone fractures, skeletal-related events, or to reduce bone loss or increase bone mass in patients with osteoporosis.

In other embodiments, the methods are used to treat, prevent or delay the onset of, glucocorticoid-induced osteoporosis (GIO) or skeletal-related events in men and women, particularly in those who are either initiating or continuing systemic glucocorticoid treatment (e.g., daily dosage equivalent to 7.5 mg or greater of prednisone) for chronic diseases. The method comprises a step of administering a compound of Formula (I) (e.g., tris(8-quinolinolato)gallium (III)) to a patient in need of such treatment, prevention or delay.

In yet some other embodiments, the methods are applied to treat, prevent or delay the onset of, or reduce the risk of, osteoporosis, particularly bone loss or bone fractures or skeletal-related events in patients receiving hormone-deprivation therapy for either prostate or breast cancer, by administering a compound of Formula (I) (e.g., tris(8-quinolinolato)gallium(III)) to such patients.

In yet some other embodiments, the methods are applied to treat, prevent or delay the onset of, or reduce the risk of, osteoporosis or low bone mineral density or bone loss or skeletal-related events such as bone fractures, associated with cancer (e.g., lung cancer, breast cancer, prostate cancer, lymphoma, multiple myeloma or neuroendocrine tumors). In particular, the compounds used in the present invention can be administered to patients identified as having cancer (e.g., lung cancer, breast cancer, prostate cancer, lymphoma, multiple myeloma or neuroendocrine tumors), either with or without bone metastasis, thereby treating, preventing or delaying the onset of, or reducing the risk of, osteoporosis, particularly bone loss, low bone mineral density, bone fractures, or skeletal-related events (e.g., severe bone pain, pathological fracture, spinal cord compression). In particular, neuroendocrine tumors often result in abnormal parathyroid hormone levels, and are thus frequently associated with low bone mineral density, bone loss, osteoporosis or skeletal-related events. Thus, in specific embodiments, the present invention provides a method of treating, preventing, or reducing the risk or incidence of, low bone mineral density, bone loss, osteoporosis or skeletal-related events (such as bone fractures) in patients having neuroendocrine tumors.

In addition, the present invention is also useful in treating or delaying the onset of any localized bone loss, e.g., associated with periodontal disease, with bone fractures, with periprosthetic osteolysis.

In yet another embodiment, the present invention is used for treating or preventing Paget's disease by administering to a patient in need of treatment a therapeutically effective amount of a compound according to Formula (I) below or a pharmaceutically acceptable salt thereof (e.g., tris(8-quinolinolato)gallium(III)).

Moreover, inhibition of osteoclasts and bone resorption can result in prevention or inhibition of tumor cell migration to bone and tumor growth in bone. Therefore, the present invention also provides a method of preventing, or delaying the onset of, bone metastasis of cancer (e.g., lung cancer, breast cancer, prostate cancer, lymphoma or multiple myeloma), which comprises administering an effective amount of a compound of Formula (I) or a pharmaceutically acceptable salt thereof (e.g., tris(8-quinolinolato)gallium (III)) to a patient identified as having, or diagnosed of, cancer (e.g., lung cancer, breast cancer, prostate cancer, lymphoma or multiple myeloma) but without bone metastasis, thereby preventing or delaying the onset of cancer bone metastasis, and/or prolonging bone metastasis-free survival. In one embodiment, the method further includes a step of identifying a patient having cancer (e.g., lung cancer, breast cancer, prostate cancer, lymphoma, multiple myeloma) but without bone metastasis.

In addition, a method of treating a cancer with bone metastasis is also provided, comprising identifying a patient having a cancer (e.g., lung cancer, breast cancer, prostate cancer, lymphoma or multiple myeloma) that has metastasized to bone, and administering a therapeutically effective amount of a compound of Formula (I) or a pharmaceutically acceptable salt thereof (e.g., tris(8-quinolinolato)gallium (III)) to the patient.

In accordance with the methods of the present invention, a therapeutically effective amount of a compound of Formula (I) or a pharmaceutically acceptable salt thereof (e.g., tris(8-quinolinolato)gallium(III)) can be used alone as a single agent, or alternatively in combination with one or more other agents (e.g., anti-cancer agents and anti-osteoporosis agents). For example, the compound of the present invention may be administered to patients who also receive supplemental calcium and/or vitamin D.

As used herein, the phrase "treating . . . with . . . " means either administering a compound to a patient or causing the formation of a compound inside a patient.

In accordance with the present invention, it is provided a use of a compound having a compound of Formula (I) or a pharmaceutically acceptable salt thereof (e.g., tris(8-quinolinolato)gallium(III)) for the manufacture of a medicament useful for reducing osteoclastic bone resorption, and for treating or preventing osteoporosis, low mineral density or skeletal-related events such as bone fractures.

The pharmaceutical compounds of Formula (I) can be administered through intradermal, intramuscular or intravenous injection, or oral administration or any other suitable means at an amount of from 0.01 mg to 1000 mg per kg of body weight of the patient based on total body weight. The active ingredients may be administered at predetermined intervals of time, e.g., four times a day. It should be understood that the dosage ranges set forth above are exemplary only and are not intended to limit the scope of this invention. The therapeutically effective amount of the active compound can vary with factors including, but not limited to, the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For example, the compound tris(8-quinolinolato)gallium (III) can be orally delivered in the form of enclosed gelatin capsules or compressed tablets. Capsules and tablets can be prepared in any conventional techniques with suitable pharmaceutically acceptable carriers such as binders, excipients, lubricants, and sweetening or flavoring agents.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil. Injectable forms are generally known in the art, e.g., in buffered solution or suspension.

In accordance with another aspect of the present invention, a pharmaceutical kit is provided comprising in a container a unit dosage form of a compound of Formula (I) or a pharmaceutically acceptable salt thereof (e.g., tris(8-quinolinolato)gallium(III)); and optionally instructions for using the kit in the method in accordance with the present invention. As will be apparent to a skilled artisan, the amount of a therapeutic compound in the unit dosage form is determined by the dosage to be used on a patient in the method of the present invention. In the kit, for example, tris(8-quinolinolato)gallium(III) can be in tablet or capsule or any other suitable form at an amount of, e.g., 0.01 mg to about 3000 mg per unit dosage form.

EXAMPLES

1. In Vitro Effects of
Tris(8-quinolinolato)gallium(III) on Osteoclasts

Mouse bone marrow cells were flushed out from femora and tibiae of two 1-2-month old mice (C57BL/6), plated in culture medium (alpha MEM supplemented with 10% heat-inactivated fetal bovine serum, 100 international units/ml penicillin, 100 µg/ml streptomycin, and 2 mM L-glutamine) in a 100-mm dish, and incubated at 37° C. in 5% $CO_2$ overnight. The next day, the non-adherent cells were pelleted and seeded at a density of 200,000 cells/$cm^2$. Then the osteoclast precursors were cultured in the presence of sRANKL (30 ng/ml) and M-CSF (30 ng/ml), and were treated with either tris(8-quinolinolato)gallium(III) or $GaNO_3$ or DMSO (as a control). The medium was changed at day 3 to obtain mature osteoclasts at day 6. For treatment with tris(8-quinolinolato)gallium(III), a drug stock solution prepared by dissolving tris(8-quinolinolato)gallium(III) in DMSO was added to the cell cultures to arrive at final concentrations of 0.2 nM, 2 nM, 0.02 µM, 0.2 µM, 2 µM, 20 µM, 50 µM, or 100 µM. At the end of the treatment, the osteoclast preparations were stained for TRAP activity using a leukocyte acid phosphatase kit from Sigma and counted for TRAP-staining multinucleated cells. Specifically, TRAP staining was performed and five areas of each well were photographed. The number of cells having more than 3 nuclei was counted. FIG. 1 shows that treatment with tris(8-quinolinolato)gallium(III) significantly inhibits the fusion of osteoclast precursors into multinucleated cells, and thus inhibits osteoclast differentiation/formation (Mean±SD of three samples; $p<0.05$ compared with DMSO and $GaNO_3$ (3.9 µM, 39 µM)).

Figure 2:
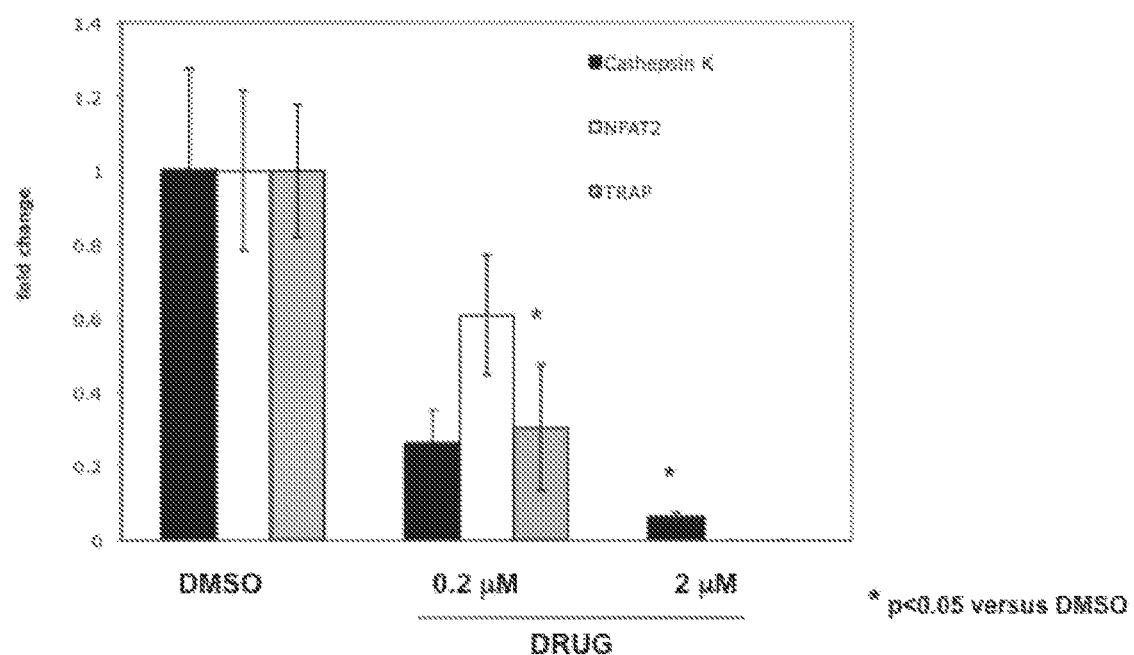
FIG. 2 shows tris(8-quinolinolato)gallium(III) ("drug") significantly inhibited cathepsin K, NFAT2 and TRAP gene expression.

RNA was also isolated for gene expression analysis of osteoclast marker genes (TRAP, cathepsin K and NFAT2). Total RNA was extracted from osteoclasts treated with DMSO or tris(8-quinolinolato)gallium(III), and mRNAs were measured using real time RT-PCR. The relative levels of mRNAs were normalized to β-actin and then expressed as fold stimulation over DMSO-treated cells. FIG. 2 shows tris(8-quinolinolato)gallium(III) ("drug") significantly inhibited cathepsin K, NFAT2 and TRAP gene expression.

In conclusion, tris(8-quinolinolato)gallium(III) is very effective in inhibiting osteoclast differentiation/maturation.

2. In Vivo Effects of
Tris(8-quinolinolato)gallium(III)

Figure 3:
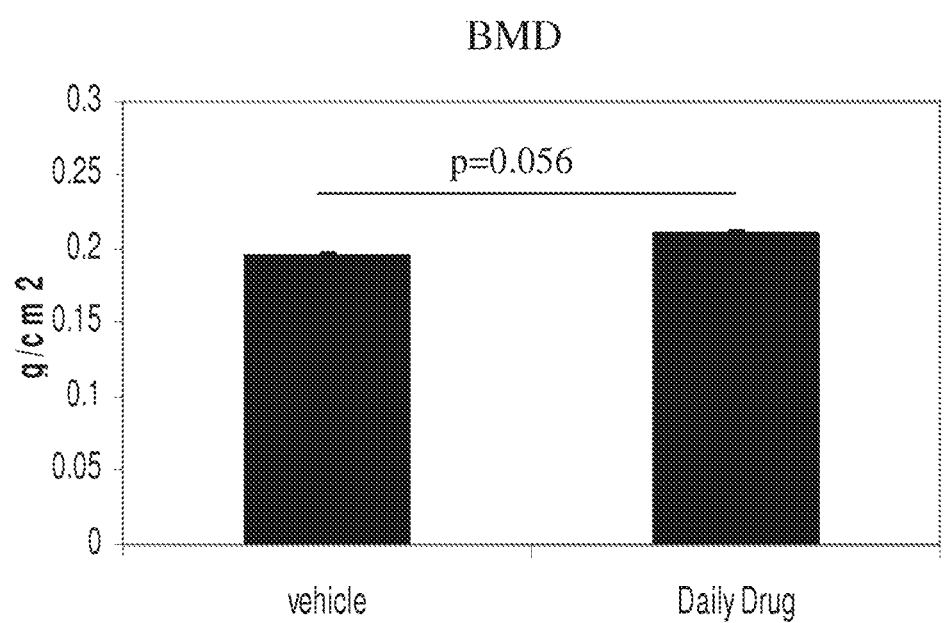
FIG. 3 is a bar graph showing daily administration of tris(8-quinolinolato)gallium(III) ("daily drug") in ovariectomized rats was associated with increased bone mineral density when compared to ovariectomized untreated rats.

The Sprague-Dawley female rats (100-125 gram, about 12 weeks old) were purchased from Taconic (Hudson, N.Y.). They were divided into 5 groups of 8 rats each. Four groups were ovariectomized, and one group was sham-operated. The rats were treated in the following manner: Group 1 ovariectomized rats were orally administered day one through day five of each week with 15 mg/kg tris(8-quinolinolato)gallium(III) ("daily"); Group 2 ovariectomized rats were treated with 75 mg/kg tris(8-quinolinolato)gallium(III) on day one of each week ("weekly"); Group 3 ovariectomized rats were treated with 38 mg/kg $Ga(NO_3)_3$ on day one of each week ("weekly"); Group 4 ovariectomized rats were treated with vehicle only (0.1% carboxymethylcellulose); Group 5 rats were sham-operated and were administered with vehicle only (0.1% carboxymethylcellulose). At the end of the experiment (32 days after the first administration of the compounds), the animals were anesthetized. Areal bone mineral density (BMD) and bone mineral content (BMC) were measured for the tibiae by dual-energy X-ray absorptiometry using an X-ray pixiMUS mouse densitometer. As shown in FIG. 3, daily administration of tris(8-quinolinolato)gallium(III) ("daily drug") to ovariectomized rats was associated with increased bone mineral density when compared to ovariectomized untreated rats ("vehicle").

Figure 4:
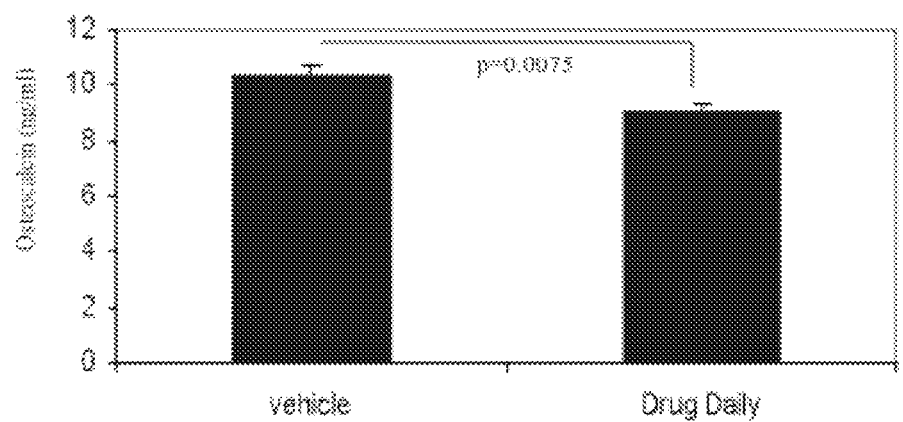
FIG. 4 is a bar graph showing that tris(8-quinolinolato)gallium(III) treatment ("drug daily") in ovariectomized rats was significantly associated with reduced serum osteocalcin when compared to ovariectomized untreated rats.

Blood was drawn from the rats and left at room temperature for at least 30 minutes before centrifuging at 200×g for 10 minutes to separate sera. Serum was used for the measurement of serum markers including osteocalcin. Osteocalcin was measured by ELISA. Osteocalcin is produced only by osteoblast in the course of bone remodeling. It is the most abundant non-collagenous protein of the bone extracellular matrix. See Weinreb, M., Shinar, D. & Rodan, G. A. *J. Bone Miner. Res.* 5, 831-842 (1990). It has been shown that osteocalcin-deficient mice exhibit higher bone mass and bones of improved functional quality. Ducy et al., *Nature.* 382, 448-452 (1996). Osteocalcin is thus a negative regulator of bone formation, and reduction of serum osteocalcin can lead to increased bone mass. As shown in FIG. 4, treatment of ovariectomized rats with tris(8-quinolinolato) gallium(III) ("drug daily") was significantly associated with reduced serum osteocalcin when compared to ovariectomized rats treated with vehicle only ("vehicle"). Thus, this further confirms that tris(8-quinolinolato)gallium(III) is useful for osteoporosis treatment.

3. Quantitative Effects of Tris(8-quinolinolato)gallium(III) in Bone Models

Mouse bone marrow cells derived as described in section 2 is plated onto 16-well BD BioCoat™ Osteologic™ Discs seeded at a density of 200,000 cells/cm² in culture medium plus sRANKL (30 ng/ml) and M-CSF (30 ng/ml). Cells are treated with varying concentrations of tris(8-quinolinolato)gallium(III) (0.0002, 0.002, 0.02, 0.2, 2, 20 µM). Similar medium changes are performed every 2 days until day 8 for quantitation of resorption areas using SPOT Advanced software by microscopy.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. The mere mentioning of the publications and patent applications does not necessarily constitute an admission that they are prior art to the instant application.

Although the foregoing invention has been described in some detail by way of illustration and example for purposes of clarity of understanding, it will be apparent that certain changes and modifications may be practiced within the scope of the appended claims.

What is claimed is:

1. A method for treating bone metastasis of cancer in a patient, comprising identifying a patient diagnosed with lung cancer, breast cancer, prostate cancer, lymphoma or multiple myeloma, and administering to said patient an effective amount of a compound of Formula (I) or a pharmaceutically acceptable salt thereof

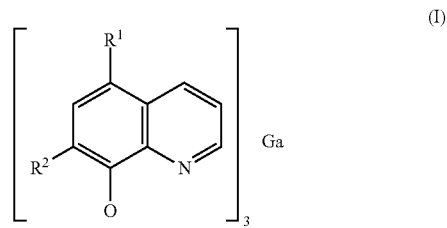

wherein $R^1$ represents hydrogen, a halogen or a sulfono group $SO_3M$, in which M is a metal ion, and $R^2$ represents hydrogen, or $R^1$ is Cl and $R^2$ is I, thereby treating the bone metastasis in said patient.

2. The method of claim 1 wherein $R^1$ and $R^2$ are H.

* * * * *